United States Patent [19]

Wegner

[11] 4,414,329

[45] Nov. 8, 1983

[54] BIOCHEMICAL CONVERSIONS BY YEAST FERMENTATION AT HIGH CELL DENSITIES

[75] Inventor: Eugene H. Wegner, Bartlesville, Okla.

[73] Assignee: Phillips Petroleum Company, Bartlesville, Okla.

[21] Appl. No.: 316,164

[22] Filed: Oct. 29, 1981

Related U.S. Application Data

[63] Continuation-in-part of Ser. No. 110,457, Jan. 15, 1980, abandoned, which is a continuation-in-part of Ser. No. 29,418, Apr. 12, 1979, abandoned.

[51] Int. Cl.$^3$ ............................................. C12P 21/00
[52] U.S. Cl. ...................................... 435/68; 435/248; 435/249; 435/255; 435/923; 435/924; 435/930; 435/938; 435/940; 435/944
[58] Field of Search .................. 435/68, 241, 247–249, 435/255, 315, 930, 938, 923–924, 940, 944

[56] References Cited

U.S. PATENT DOCUMENTS

| | | |
|---|---|---|
| 3,355,296 | 11/1967 | Perkins et al. |
| 3,607,652 | 9/1971 | Ueda |
| 3,616,249 | 10/1971 | Cavallo |
| 3,647,632 | 3/1972 | Johnson et al. ................. 435/315 X |
| 3,733,253 | 5/1973 | Suzuki et al. |
| 3,773,620 | 11/1973 | Kimura et al. |
| 3,844,893 | 10/1974 | Hitzman |
| 3,862,006 | 1/1975 | Abe et al. |
| 3,879,261 | 4/1975 | Matsumoto |
| 3,981,774 | 9/1976 | Hitzman |
| 3,982,998 | 9/1976 | Hitzman et al. ................ 435/804 X |
| 3,982,998 | 9/1976 | Hitzman et al. |
| 4,062,727 | 12/1977 | Srinivasan et al. ............. 435/804 X |
| 4,169,010 | 9/1979 | Marwil ............................. 435/804 X |
| 4,226,939 | 10/1980 | Wegner |
| 4,261,420 | 4/1981 | Hitzman |
| 4,282,328 | 8/1981 | Fukuda et al. |
| 4,284,724 | 8/1981 | Fukuda |

FOREIGN PATENT DOCUMENTS

| | | |
|---|---|---|
| 670301 | 9/1963 | Canada |
| 671312 | 10/1963 | Canada |
| 817868 | 7/1969 | Canada |
| 900392 | 5/1972 | Canada |
| 925037 | 4/1973 | Canada |
| 946769 | 5/1974 | Canada |
| 1014879 | 8/1977 | Canada |
| 2407740 | 8/1974 | Fed. Rep. of Germany |
| 2006235 | 12/1969 | France |
| 1210770 | 10/1970 | United Kingdom |

OTHER PUBLICATIONS

Ajinomoto "Preparation of Yeast Cells" Chemical Abstracts, vol. 73, Abstract No. 86563e (1970).

Omato et al. "Yeast Cultivation Based on Ethanol" Chemical Abstracts, vol. 76, Abstract No. 71037x (1972).

Kitagaki et al. "Cultivation of Yeast" Chemical Abstracts, vol. 81, Abstract No. 24188r (1974).

International Association of Microb. Soc. XII International Congress Munchen, Sep. 3–8, 1978, Abstract Nos. 40.6, 40.7, 40.8 and 40.9.

Kuraishi et al. "Study of Internal Structure of Air Lift Fermenter in Production of Methanol SCP" Proc. Int'l Sym. Microbial Growth, Japan 1975.

Hazeu et al. Arch. Mikrobiol. vol. 87 (1972) pp. 185–188.

Levine et al. Applied Microbiology, vol. 26, Dec. 1973, pp. 982–990.

Fonken et al. "Chemical Oxidations with Microorganisms" Marcel Dekker, Publishers, N.Y., 1972, pp. 113–115.

*Primary Examiner*—R. B. Penland

[57] ABSTRACT

A method of high cellular density yeast fermentation at high mineral salts feed to and maintained in the ferment.

Single cell protein (SCP) is produced in an aerobic fermentation process at high yields under high cell density conditions employing media of high mineral salts concentration. Novel *Pichia pastoris* and *Hansenula polymorpha* yeasts are disclosed.

58 Claims, No Drawings

BIOCHEMICAL CONVERSIONS BY YEAST FERMENTATION AT HIGH CELL DENSITIES

This application is a continuation-in-part of application Ser. No. 110,457 filed Jan. 15, 1980, now abandoned, which is a continuation-in-part of application Ser. No. 29,418 filed Apr. 12, 1979, now abandoned.

FIELD OF THE INVENTION

The invention pertains to biochemical conversions. In one aspect, the invention relates to single cell protein. In another aspect, the invention pertains to the production of single cell protein. In a further aspect, the invention pertains to novel yeast strains. In yet another aspect, the invention pertains to chemical conversions by microbiological action.

BACKGROUND OF THE INVENTION

Efforts to relieve world-wide shortages of protein have included various bio-synthesis processes in which single cell protein (SCP) is obtained by the growth of one or another of a variety of microogranisms on various carbon-containing substrates.

The carbon energy substrates should be readily available, relatively cheap, uniform, and safe. Petroleum hydrocarbons have been employed as carbon energy source, but have faced practical difficulties in the lack of water-solubility and in the high consumption of molecular oxygen needed to assist in the microbial conversion. Other processes have centered on the use of oxygenated hydrocarbon derivatives as feedstocks due to their relative water-solubility and hence ease of handling in an aqueous ferment, and in the substantially reduced molecular oxygen requirements for the microbial conversion-growth process.

However, a limiting factor in the commercialization of single cell protein processes has been the necessity to control the ferment at relatively moderate cell densities, with but moderate yields of dried cells based on substrate consumed, and the consequent necessity to handle large amounts of total fermentation effluent liquor in order to recover the moderate amounts of SCP material. Handling large quantities of aqueous fermentation effluent liquor complicates concentration of the single cell protein product in such as centrifuges, as well as washing and drying steps.

Some processes in the past have concentrated on the culturing of bacteria because of the slightly higher crude protein contents of the cell as compared to the content obtainable from yeast in general. However, yeasts are widely available and relatively simply cultured. Yeast cells generally are slightly larger as compared to bacteria cells, and, hence, yeast cells tend to be more easily separated from the fermentation effluent liquor.

Discovery of means and methods to increase cell yields, and particularly to operate and maintain continuous production at high cell densities, would be highly desirable. The resultant handling of substantially less fermentation liquor effluent volume, for example, would mean large savings in reduced sizes of piping and pumps, reduced makeup water requirements with reduced sterilization requirements, and reduced requirements of equipment sizing and handling for coagulation and separation processes.

Growth of yeast cells at high cell densities further allows more efficient assimilation of substrate in a smaller fermentation apparatus, useful, for example, in an effluent scrubbing scheme such as disclosed in U.S. Pat. No. 3,646,239. Yeast cells grown at high cell densities produce extracellular products in excellent yields, useful, for example, in an enhanced oil recovery process such as disclosed in U.S. Pat. No. 4,261,420, wherein a high cell density fermentation process will provide maximum $CO_2$ production for oil recovery purposes. Other biochemical conversions using yeasts which can benefit from the high cell density fermentation process of my invention include the oxidation of alkanes to dicarboxylic acids (U.S. Pat. No. 3,796,630), the oxidation of $C_{14}$ to $C_{18}$ 1-alkanes to epoxides and glycols Fonken, G. S., and R. a. Johnson, *Chemical Oxidations With Microorganisms* (Dekker, N.Y., 1972) pp 113-115, the oxidation of alcohols to ketones (U.S. Pat. No 4,250,259, U.S. Pat. Nos. 4,268,630 and 4,269,940), and the production of extracellular biopolymers for use as viscosifying agents in aqueous media, e.g. in oil field water flooding applications (U.S. Pat. No. 3,312,279); the disclosures of all of these patents/articles being herein incorporated in total by reference, since all are amenable to improvement by my high salts feed/high cellular density fermentation method.

SUMMARY OF THE INVENTION

I have discovered a method which enables yeast-fermentations to be conducted at very high cellular densities, continuously, by a high salts feed method. My method of imposing a high salts force feed to the ferment results in a high cellular density of yeast cells contained in the ferment. My high salts/high cell density method is effective, and maintains high cell densities without the heretofore art taught necessity of physical means of cellular build-up by either removing ferment and separating cells for recycle to the fermentor, or to use an internal separator in the fermentor in order to separate out liquor for removal and thus build up cell counts, either method being expensive, difficult, at times harmful to the cells, lacking adequate ease of control, and add markedly to the apparatus costs.

My method of high cell density fermentation results in high rate usage of substrate, high (bio) chemical conversions, and desirable levels of extracellular products production.

I have discovered a way to operate a continuous aerobic fermentation process employing yeast cultures so as to enable operation of the ferment in the fermentor at very high cell densities ordinarily unobtainable. My method achieves high levels of substrate utilization by adding media containing high mineral salts concentrations to the ferment in the fermentor. This enables high yields of yeast single cell protein and for high levels of extracellular product formation.

Cell density is defined as the concentration of cells by weight on a dry basis per volume of ferment. The ferment is defined as the total volume of aqueous fermentation broth or liquor, including cells. Cell density usually is expressed as grams/liter. Yield is defined as the amount of cells by weight produced for a given consumption by weight of carbon energy source or substrate fed to the ferment, and is usually expressed in grams/gram.

The high cell densities obtainable by my process significantly streamline and reduce the cost of single cell protein production, and of chemical conversion promoted by yeasts. Concentrating the resulting single cells as protein product by such as centrifuge means in many instances is sharply reduced or even eliminated. The cellular product (cells) can be, if desired, washed in washing means to remove residual unconsumed salts and extra-cellular products such as amino acids, biopolymers extracellular enzymes, and the like. The washed cells can then be sent directly to a dryer means such as a spray dryer. The washings contain most of the remaining mineral salts not incorporated into the cells and the extracellular products. The washings can be treated to recover or isolate extracellular products such as the biopolymers, enzymes, etc., and the unconsumed salts can be recycled to the fermentor as may be appropriate.

Requirements for water to the fermentation step thus are reduced considerably, and, importantly, there is little or no waste water requiring disposal. Alternatively, if desired, the total ferment including residual salts and extracellular products can be dried.

Heretofore, continuous processes for the production of single cell protein materials from yeast cultures typically gave ferment effluents of relatively low yeast cell contents, such as about 20 to 25 grams of celles per liter of ferment. My invention, however, provides a process whereby the fermentation step produces yeast cells at relatively very high cell density levels, such as above 100 grams per liter of ferment. Such high cell densities in the ferment, coupled with high yields of yeast cells, mean more efficient effective production of yeast cells and extracellular products, as well as more efficient utilization of substrate, particularly under continuous production conditions.

HIGH SALTS/HIGH CELL DENSITY APPLICATIONS

Hereinabove, I have described, with regard to my high salts/high cell density fermentation invention, various applications of my invention to both production of single cells to obtain cellular protein and enzymes as well as various extracellular products, and to various biochemical conversions. Where the biochemical conversion is the prime objective, the coproduced cells may in a sense be incidental or a by-product.

My invention is applicable to any process using appropriate yeasts in an aqueous aerobic fermentation process to achieve, by the yeasts or their enzymes, a biochemical conversion. These include the oxidation to carbon dioxide of a variety of substrates such as the alcohols; biomass to alcohol; oxygenated hydrocarbons to biopolymers suitable for viscosifiers or drilling fluids; production of amino acids; of phosphomannan gums (phosphorylated mannan) from glucose (See U.S. Pat. No. 3,312,279); biocellulose; conversion of hydrocarbons to alcohols, ketones and/or organic acids; alkenes to glycols and epoxides; alcohols to ketones; production of variety of medicines as extracellular products; and others. Even old yeast fermentation processes such as conversion of sugars to alcohols, or to acids can be conducted more efficiently in smaller equipment by my high salts/high cell density method. Refer for example to Oura, *Process Biochemistry*, April 1977, pp 19-21 and 35; and Perlman, Chemtech, April 1974, pp 210-215.

DETAILED DISCLOSURE OF THE INVENTION

In accordance with my invention, yeasts are grown under substantially continuous aerobic aqueous fermentation conditions on a suitable carbon energy source as substrate, employing effective amounts of molecular oxygen-containing gases, assimilable-nitrogen source, high input of nitrient mineral salts, and, where necessary, adding additional nutrient organic material such as vitamins such as biotin and/or thiamine.

In my process the mineral salts are added at high levels as will be described hereinafter, resulting in a continuous fermentation process operating at high cell densities, with high yields.

My invention essentially lies in almost the force-feeding of the cells by adding highly concentrated (relatively) mineral salts into the ferment, resulting in high growth rates of the yeast. The mineral salts concentration in the liquid supernatant of the ferment (that is, the ferment excluding cells) itself remains, of course, at relatively low levels, since the salts are consumed by the yeast cells in growth and reproduction. The salts concentration in the cells plus liquid supernatant, thus, is very high in my process.

FERMENTATION CONDITIONS

Culturing is accomplished in a growth medium comprising an aqueous mineral salts medium, the carbon energy source material, molecular oxygen, assimilable nitrogen, and of course, a starting inoculum of one or more particular species of yeast microorganisms to be employed.

In my invention, high concentrations of mineral salts are fed to the ferment and high concentrations are maintained in the ferment. It is necessary to supply suitable amounts in proper proportions of selected mineral nutrients in the feed media, in order to assure proper microorganism growth, to maximize assimilation of the carbon and energy source by the cells in the microbial conversion process, and to achieve maximum cellular yields with maximum cell density in the fermentation media.

Although the composition of the ferment can vary over a wide range, depending in part on the yeast and substrate employed, the minerals content in the ferment (that is, liquid plus cells) in accordance with my invention is relatively high, at higher levels than heretofore considered suitable or practiced by the prior art. Set forth in the table below are the minimum, broad, and presently preferred ranges of concentrations of various elements in the ferment, the concentration being expressed as of the element, though it is recognized that all or part of each can be present in the form of a soluble ion, or in cases such as P are present in a combined form of some type such as phosphate. The amount of each element is expressed in grams or milligrams per liter of ferment (aqueous phase, including cells):

TABLE I

| | Weight of Element per Liter of Ferment | | |
|---|---|---|---|
| Element | Minimum | Broad Range | Preferred Range |
| P | 1.9 g | 2.9-20 g | 2.2-10 g |
| K | 1 g | 1-20 g | 1.5-10 g |
| Mg | 0.15 g | 0.15-3 g | 0.3-1.2 g |
| Ca | 0.06 g | 0.06-1.6 g | 0.08-0.8 g |
| S | 0.1 g | 0.1-8 g | 0.2-5 g |
| Fe | 6 mg | 6-140 mg | 9-80 mg |
| Zn | 2 mg | 2-100 mg | 3-40 mg |
| Cu | 0.6 mg | 0.6-16 mg | 1-10 mg |
| Mn | 0.6 mg | 0.6-20 mg | 0.9-8 mg |

Sulfur desirably is employed in the form of sulfate. Some of the metals required are advantageously added in the form of a sulfate, so that the minimum concentrations of sulfur normally are exceeded. Any or all of the metals listed can be used or present as the sulfate. Preferably, the magnesium, calcium, iron, zinc, copper, and manganese are employed in the form of a sulfate or chloride, or in the form of a compound which is converted in situ to a sulfate or chloride. The potassium preferably is employed as a sulfate, chloride, or phosphate or in the form of a compound which is converted in situ to a sulfate, chloride, or phosphate. The phorphorus preferably is employed in the form of phosphoric acid or in the form of a phosphate, monohydrogen phosphate, or dihydrogen phosphate, e.g., as a potassium or ammonium salt, or as a compound which is converted in situ to such a salt.

Conveniently, a primary mineral salts medium can be employed to include the nutrients comprising P, K, Mg, S, and Ca; and a trace mineral medium to supply nutrients comprising Fe, Zn, Mn, and Cu.

Other elements which may be present, at least in trace amounts, include such as sodium and cobalt, e.g., as a halide or sulfate; molybdenum, e.g., as molybdate; boron, e.g., as borate; selenium, e.g., as selenite or selenate; or iodine, e.g., as iodide.

In typical high cell density fermentation, the ferment will comprise about one-half supernatant medium and one-half yeast cells, by volume. These one-half by volume yeast cells, however, will contain at least about two-thirds of the mineral salts content of the ferment (liquid plus cells).

YEAST

According to my process, I employ a culture of a yeast suitable for growth on carbon-containing substrates under aqueous fermentation conditions. Suitable yeasts include species from the genera Candida, Hansenula, Torulopsis, Saccharomyces, Pichia, Debaryomyces, and Brettanomyces. The presently preferred genera include Candida, Hansenula, Torulopsis, Pichia, and Saccharomyces. Examples of suitable species include:

| | |
|---|---|
| Brettanomyces petrophilium | Pichia farinosa |
| Candida boidinii | Pichia polymorpha |
| Candida lipolytica | Pichia membranaefaciens |
| Candida mycoderma | Pichia pinus |
| Candida utilis | Pichia pastoris |
| Candida stellatoides | Pichia trehalophila |
| Candida robusta | Saccharomyces cerevisiae |
| Candida claussenii | Saccharomyces fragilis |
| Candida rugosa | Saccharomyces rosei |
| Candida tropicalis | Saccharomyces acidifaciens |
| Debaryomyces hansenii | Saccharomyces elegans |
| Hansenula minuta | Saccharomyces rouxii |
| Hansenula saturnus | Saccharomyces lactis |
| Hansenula californica | Torulopsis sonorensis |
| Hansenula mrakii | Torulopsis candida |
| Hansenula silvicola | Torulopsis bolmii |
| Hansenula polymorpha | Torulopsis versatilis |
| Hansenula wickerhamii | Torulopsis glabrata |
| Hansenula capsulata | Torulopsis molishiana |
| Hansenula glucozyma | Torulopsis nemodendra |
| Hansenula henricii | Torulopsis nitratophila, |
| Hansenula nonfermentans | Torulopsis pinus, and |
| Hansenula philodenra | Torulopsis bombicola |
| Hansenula holstii. | |

If desired, mixtures of two or more species of yeasts can be employed. The particular yeast employed depends in part on the carbon-containing substrate to be used since it is well known that different yeasts often require somewhat different substrates for best growth; or, that specific biochemical conversions are best conducted by specific yeast genera or species. For example, it is recognized that some particular strains of species listed above, such as of *Pichia pastoris*, do not grow on methanol, i.e., do not utilize methanol.

It should be kept in mind that the utilization of yeasts for various chemical conversions sometimes is considered in a simplistic fashion as merely full or partial oxidation. In fact, however, yeast conversion of the various possible substrates involves complex and complicated enzymatic conversion pathways through a variety of intermediates. Hence, the beauty and variety of aqueous biochemical/enzymatic conversions is very large. My high salts/high cell density method improves all yeast-based conversions.

Presently preferred for single cell protein production are those *Pichia pastoris* and *Hansenula polymorpha* which do grow suitably on oxygenated-hydrocarbon feedstocks, particularly, a lower alcohol such as methanol. Presently preferred are the particular strains designated as, or which are derived from, the strains deposited as *Pichia pastoris* (Culture 21-2) NRRL Y-11431, *Pichia pastoris* (Culture 21-1) NRRL Y-11430, *Hansenula polymorpha* NRRL Y-11170, and *Hansenula polymorpha* (Culture 21-3) NRRL Y-11432, since I have found these strains to be particularly suitable for use in producing SCP protein materials at high cell densities with high yields. This feature of these strains of *Pichia pastoris* (Culture 21-2) NRRL Y-11431 and *Pichia pastoris* (Culture 21-1) NRRL Y-11430 is considered particularly unusual for these species since out of four *Pichia pastoris* cultures tested, only two would grow on methanol at all. I consider *Pichia pastoris* (Culture 21-2) NRRL Y-11431, *Pichia pastoris* (Culture 21-1) NRRL Y-11430, and *Hansenula polymorpha* (Culture 21-3) NRRL Y-11432, also to be novel and unique. *Pichia pastoris* NRRL Y-11430 and Y-11431 further are particularly preferred for use when the coproduction of a particularly useful alcohol oxidase also is desired.

The carbon energy substrate can be any carbon energy source, such as hydrocarbons, oxygenated hydrocarbons, including various carbohydrates, and the like, suitable as yeast substrates. It is recognized that particular yeasts do vary in their preference for various substrates.

The presently preferred substrates for aqueous fermentation conditions for yeasts are the carbon-oxygen-hydrogen significantly water-soluble compounds. The term "oxygenated hydrocarbon" is intended to be a generic term in this disclosure descriptive of compounds employable, and not necessarily a limiting term referring to the source of the substrate. For this disclosure, the oxygenated hydrocarbons include the water-soluble carbohydrates, as well as those alcohols, ketones, estes, acids, and aldehydes, and mixtures, which are reasonably significantly water-soluble in character generally of 1 to 20 carbon atoms per molecule. The more suitable oxygenated hydrocarbons are those of substantially greater water-solubility of up to about 10 carbon atoms per molecule, or are the water-soluble carbohydrates generally.

Exemplary carbohydrates include glucose, fructose, galactose, lactose, sucrose, starch, dextrin, and the like, alone or in admixture. Of the other types of oxygenated hydrocarbons, examples include methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and the like, as well as mixtures thereof.

It also is possible to employ in accordance with my process, though presently less preferred where single cells are the desired product for use for such as food because of the difficulty sometimes encountered in removing residual substrate from the single cell protein cells, normal paraffins of such as 10 to 20 carbon atoms per molecule. Yeasts generally do not assimilate paraffins of less than 10 carbon atoms per molecule. These typically include such as decane, undecane, dodecane, tridecane, tetradecane, pentadecane, hexadecane, octadecane, eicosane, and the like, and mixtures thereof.

Presently preferred for yeast cell production are the water-soluble alcohols of 1 to 4 carbon atoms, water-soluble acids of 2 to 4 carbon atoms, and the water-soluble carbohydrates. Preferred are the water-soluble monohydric aliphatic hydrocarbyl alcohols. It should be noted that 2-methyl-1-propanol is inhibitory to some yeasts, and in fermentations with such yeasts this alcohol should be avoided. Presently most preferred are the alcohols of 1 to 4 carbon atoms (other than 2-methyl-1-propanol); of these methanol and ethanol presently are preferred over the others; and methanol is the most prefered, due to the low relative cost of such feedstock.

Petroleum gases can be oxidized, and the water-soluble materials employed, such as oxidation of methane, ethane, and the like, to provide mixtures predominantly of the corresponding alcohol as well as various aldehydes, ketones, acids, and the like, and similarly suitable hydrocarbon fractions from various petroleum refinery sources produced within the integrated refining and chemical processing complex, sometimes termed a petrocomplex, can be utilized for fermentation purposes.

The salts in the supernatant are at a relatively low concentration, since there is a high take-up by the growing reproducing cells. The mineral salts in the cells may not be as fed or applied since some may be in a bound organic form. Mineral analysis of the ferment, of course, would reflect a total mineral content.

In addition to the mineral salts, vitamins (organic growth factors) can be employed in the ferment as is known in the art, when their presence is desirable for the propagation of the particular yeast chosen. For example, many yeasts for their proper propagation, seem to require the presence of one or both of the vitamins biotin and thiamine, or other medium constituents which contain these vitamins, e.g., yeast extract. Thus, for example, with a yeast such as a *Hansenula polymorpha*, it is desirable to employ biotin in an amount of about 0.04 to 0.8 milligram per liter of aqueous mineral medium and thiamine hydrochloride in an amount of about 4 to 80 milligrams per liter of aqueous mineral medium. Alternatively, all or part of the biotin and thiamine can be provided by use of yeast extract or the like.

In my application Ser. No. 875,667 filed Feb. 6, 1978, now U.S. Pat. No. 4,226,939 issued Oct. 7, 1980, I disclose that the employment of water containing residual amounts of chlorine, such as is commonly encountered in water from purification treating processes in some countries, in preparing mineral medium to which growth factors are added for use in aqueous aerobic fermentation processes tends to render ineffective the growth factors, particularly vitamins such as biotin or thiamine. I also disclose my discovery that in such fermentation system, employing an aqueous mineral medium prepared from water containing residual chlorine, that removal of the chlorine before adding the growth factors avoids the loss or deactivation of the growth factors. Thus, I also diclose methods of treating the residual chlorine-containing water so as to effectively eliminate the traces of residual chlorine therefrom and thus avoid the vitamin loss.

I have now found that water containing heretofore objectionable amounts of residual chlorine nevertheless can be utilized in fermentation processes employing vitamins yet without inactivation of the vitamins by the chlorine if the vitamins are added to the fermentation zone as a separate stream separate from the aqueous nutrient medium stream. Thus, the mineral nutrient medium can now employ make-up water even containing trace amounts of chlorine. This arrangement thus avoids the need for pre-treating, by expensive and/or time consuming methods, the water which contains residual trace amounts of chlorine.

The above-described separate addition of the vitamins to the fermentation zone is preferably and conveniently accomplished by admixing the vitamins with at least a portion of but preferably the entire carbon energy substrate stream prior to charging these materials to the fermentation zone. If an aqueous admixture of vitamins and carbon energy substrate is employed, the water used for initial dilution of the vitamins should preferably be free of traces of residual chlorine, such as deionized water, to avoid any premature loss before mixing with the aqueous carbon substrate stream such as methanol-in-water.

If desired, and also preferred, an admixture can be made of water and a water-soluble carbon substrate such as methanol, such as about 20 volume percent methanol in water, and then the vitamins can be dissolved in the methanol-in-water solution, and fed then to the fermentor. By this mode, residual chlorine need not be first removed, but yet the vitamins are fully preserved.

In a more preferred embodiment, the separate addition of vitamins to the fermentation zone is accomplished utilizing an admixture of vitamins, at least a portion of the carbon energy substrate as noted above and the further addition of an aqueous trace mineral salts solution. The trace mineral salts comprise what has been referred to hereinabove as the trace elements such as cobalt, molybdenum, boron, selenium, iodine, as well as manganese, copper, zinc, and iron. The use of this more preferred embodiment not only avoids the vitamin inactivation problem caused by traces of chlorine in the water used for the aqueous mineral salts medium, but also avoids another problem that is often encountered in the fermentation processes. This problem is the formation of precipitates in the heat sterilization zone employed to treat the aqueous mineral salts medium, requiring frequent cleaning. The presence of the trace mineral salts in its usual admixture with the primary mineral nutrient salts apparently promotes the formation of troublesome precipitates in the heat sterilization zone. Thus, by not including the trace mineral salts in the aqueous mineral salts medium stream, but rather instead charging the trace mineral salts in admixture with the vitamins and at least a portion of the carbon energy substrate solves two very troublesome problems. As noted above, the water used to prepare the admixture of trace mineral salts, at least a portion of the carbon energy substrate, and the vitamins should preferably be free of residual traces of chlorine.

The stream comprised of vitamins, a portion of the carbon energy substrate, and trace minerals can be sterilized by filtration if desired. However, it is preferable and convenient to combine said stream with the major carbon energy substrate stream prior to charging to the fermentation zone and filtering the entire combined streams just prior to chargint to the fermentation zone.

The fermentation itself is an aerobic aqueous process requiring molecular oxygen which is supplied by a molecular oxygen-containing gas such as air, oxygen-enriched air, or even substantially pure molecular oxygen, so as to maintain the ferment with an oxygen partial pressure effective to assist the microorganism species in growing or in biochemically converting substrate in a thriving fashion. By using an oxygenated hydrocarbon substrate, the total oxygen requirements for growth or substrate conversion of the microorganism are reduced from the requirements when a paraffin is used. Even so, adequate quantities of molecular oxygen must be supplied for growth, since the assimilation and/or bioconversion of the substrate and corresponding growth of the microorganism is, in part, a combustion process.

The rate at which molecular oxygen is supplied to the forment should be such that the growth of the yeast or substrate conversion is not limited by lack of oxygen. Fermentor designs vary widely in their ability to transfer oxygen to the culture. Although the overall aeration rates can very over a considerable range, with fermentors that are very efficient in oxygen transfer aeration generally is conducted at a rate of about 0.5 to 8, preferably about 1 to 6, volumes (at the pressure employed and at 25° C.) of molecular oxygen-containing gas per liquid volume in the fermentor per minute. This amount is based on air of normal oxygen content being supplied to the reactor, and in terms of pure molecular oxygen the respective ranges would be about 0.1 to 1.7, or preferably about 0.2 to 1.3, volumes (at the pressure employed and at 25° C.) of molecular oxygen per liquid volume in the fermentor per minute.

The pressure employed for the microbial fermentation step can range widely. Typical pressures are about 0 to 150 psig, presently preferably about 0 to 60 psig, more preferably 35 to 40 psig, as a balance of equipment and operating costs versus oxygen solubility achieved. Greater than atmospheric pressures are advantageous in that such pressures do tend to increase the dissolved oxygen concentration in the aqueous ferment, which in turn can help increase cellular growth rates. At the same time this is counterbalanced by the fact that high pressures do increase equipment and operating costs.

The fermentation temperature can vary somewhat, but generally will be about 25° C. to 65° C., generally preferalby about 28° C. to 50° C. The yeast cultures *Pichia pastoris* Culture 21-2 deposited as NRRL Y-11431 and *Pichia pastoris* Culture 21-1 deposited as NRRL Y-11430 generally prefer a ferment temperature of about 30° C. The *Hansenula polymorpha* NRRL Y-11170 and *Hansenula polymorpha* Culture 21-3 deposited as NRRL Y-11432 presently appear to prefer a ferment temperature on the order of about 38° C. to 40° C.

Yeasts require a source of assimilable nitrogen. The assimilable nitrogen can be supplied by any nitrogen-containing compound or compounds capable of releasing nitrogen in a form suitable for metabolic utilization by the yeast microorganism. While a variety of organic nitrogen source compounds, such as protein hydrolysates, technically can be employed, usually cheaper nitrogen-containing compounds such as ammonia, ammonium hydroxide, urea, and various ammonium salts such as ammonium phosphate, ammonium sulfate, ammonium pyrophosphate, and ammonium chloride can be utilized. Ammonia gas itself is convenient for large scale operations, and can be employed by bubbling through the aqueous microbial ferment in suitable amounts. At the same time, such ammonia also assists in pH control.

The pH range in the aqueous microbial ferment should be in the range of about 3 to 7, more preferably and usually about 3.5 to 5.5. Preferences of certain microorganisms for a pH range are dependent to some extent on the medium employed, as well as on the particular microorganism, and thus may change somewhat with change in medium as can be readily determined by those skilled in the art.

The average retention time of the ferment in the fermentor can vary considerably, depending in part on the fermentation temperature and yeast culture employed. Generally, the retention time will be about 2 30 hours, preferably presently about 4 to 14 hours, based on average retention.

High concentrations of some of the described carbon and energy substrates, particularly such as methanol or formaldehyde or the like, may be inhibitory to satisfactory microbial growth or even toxic to the microorganisms in the fermentation. Relatively high concentrations of such substrates thus should be avoided, so that it is generally desirable to maintain the substrate concentration in the ferment at a maximum tolerable level. With some of the lower alcohols, this level in the ferment generally is about 0.001 to 5 volume percent, preferably about 0.005 to 0.05 volume percent, while with the aldehydes the level should be one-tenth of these due to the toxicity of aldehydes, so as to neither starve nor inhibit the growth rates of the microorganisms chosen.

When the carbon and energy source material contains an aldehyde in amounts potentially deleterious to the microorganism, the deleterious aldehyde effects can be allievated by first treating the substrate with a suitable amount of a nitrogen-containing compound, preferably ammonia, ammonium hydroxide, or other active ammonium compound, in a ratio of about 0.01 to 10 mol equivalents of such nitrogen-containing compounds per mol of aldehyde. Such a treated substrate then is not only the carbon energy source, but also contains at least a portion of the necessary assimilable nitrogen.

Conveniently, the fermentation is conducted in such a manner that the carbon-containing substrate can be controlled as a limiting factor, thereby providing good conversion of the carbon-containing substrate to yeast cells and extracellular products, thereby avoiding potential contamination of the yeast cells with a substantial amount of unconverted substrate. The latter is not a problem with water-soluble substrates, since any remaining traces are readily washed off. It may be a problem, however, in the case of non-water-soluble substrates such as the higher n-paraffins, requiring added product treatment steps such as removal of residual hydrocarbon by suitable solvent washing steps.

Continuous operation is much to be preferred for ease of control, production of uniform quantities of either cells or extracellular products, and most economical uses of all equipment. In a continuous process, the carbon and energy source material as substrate, aqueous mineral medium, assimilable nitrogen source, and molecular oxygen-containing gases, are added continuously to the ferment in the fermentor combined with continuous withdrawal of ferment. Although the volume ratio of added carbon energy substrate:added aqueous mineral medium can vary over a wide range, depending in part on the nature of the carbon-containing substrate, generally it will be in the range of about 1:9 to 6:4, presently and preferably in the range of about 2:8 to 5:5.

One skilled in the art readily recognizes that the maximum cell density obtainable is a function of the cell yield (g of cells per g of substrate feed) and the percent substrate in the total feed to the fermentor. This, *Pichia pastoris* NRRL Y-11430, which gives approximately 40 percent yield of single cells when grown on methanol as carbon source, exhibits a maximum cell density of about 65 grams of cells per liter of ferment from a total feed including 20 volume percent methanol. Yet, with a total feed including 40 volume percent methanol, the same *Pichia pastoris* exhibits a maximum cell density of greater than 126 grams of cells per liter of ferment. Total feed is the carbon substrate plus mineral media including water.

If desired, part or all of the carbon energy source material and/or part of the assimilable nitrogen source such as ammonia can be added to the aqueous mineral medium prior to passing the aqueous mineral medium to the fermentor. Most convenient in my work in high cell density fermentations employing methanol to produce single cell protein has been the use of a feed ratio of about 40 volume percent alcohol to 60 volume percent mineral salts medium.

Each of the streams introduced into the reactor preferably is controlled at a predetermined rate, or in response to a need determinable by monitoring, such as concentration in the ferment of the carbon energy substrate, the pH, the dissolved oxygen, the cell density measurable by light transmittancy, or the like, and the oxygen or carbon dioxide in the off-gases from the fermentor. The feed rates of the various materials streams can be varied so as to obtain as rapid a cell growth rate as possible, constant with efficient utilization of the carbon and energy source, to obtain as high a yield of yeast cells and/or extracellular products, relative to substrate charge as possible, or to maximize the particular biochemical conversion being practiced. Thus, by the process of my invention, yeast cells can be obtained in yields of about 30 to 110 grams per 100 grams substrate charged, depending in part on the particular substrate used.

All equipment, reactor, or fermentation means, vessel or container, piping, attendant circulating or cooling devices, and the like, most preferably are sterilized, usually by employing steam such as at about 250° F. (121° C.) for at least about 15 minutes. The sterilized reactor is inoculated with a culture of the specified microorganism in the presence of all the required nutrients, including molecular oxygen, and the carbon-containing substrate.

The type of fermentor employed is not critical in the practice of the fermentation process of my invention, though presently preferred is operation in a foam-filled fermentor mode. A fermentor designed to encourage and maintain the produced foam usually is beneficial to the process of achieving the increased oxygen transfer necessary to maintain desired high cell densities and rapid growth rates.

The typical start-up procedure from stock culture to continuous culture may take a number of days and involve several steps. For example, the initial growth of a stock yeast culture on YM media conveniently employs a readily assimilable carbon source such as glucose, and takes about 2 days. Cells are then transferred to small flasks containing minimal nutrient medium with the desired carbon source, such as methanol or other. Usually, 2-3 days are required for this phase. Cells are then transferred into larger flasks with fresh nutrient medium and additional carbon source. About 3 more days usually are necessary for the culture to grow up in this medium. There is then enough culture to inoculate a typical 14 L laboratory fermentor.

In starting out a continuous fermentation, the aqueous mineral medium, suitable concentration of carbon source, assimilable nitrogen, trace components where desired, and the starting inoculum of the desired yeast strain, the latter selected in accordance with the type of biochemical conversion to be practiced, and grown up as described above, are placed in a sterilized fermentor, and suitable flows of oxygen and the various feeds are gradually commenced. If desired, the initial fermentation substrate can be such as glucose or glycerol, with gradual change to such as methanol as cell density builds up. It is possible to begin at low mineral salts levels in the aqueous ferment and build up to a high mineral salts level by feeding an aqueous mineral medium having a high concentration of mineral salts to the ferment, through I normally simply add high salts medium initially to the fermentor to commence immediate operation. One skilled in the art realizes that a brief lag time will usually occur at start-up before the inoculum builds up enough cells for full input of salts and substrate to be effectively utilized.

PRODUCT RECOVERY

The yeast cells produced in accordance with my high salts/high cell density process can be recovered from the fermentation admixture effluent by conventional means, such as by centrifugation or filtration. Extracellular products can be recovered from the substantially cell-free remaining supernatant liquid by conventional means. The substantially cell-free effluent can be treated, for example, with acetone or a lower alcohol such as methanol or ethanol to precipitate polymeric materials produced extracellularly. The cell-free effluent also can be treated by solvent extraction and/or base extraction to recover, if desired, other extracellular products such as pigments, vitamins, or organic acids produced during the culturing process. The cell-free effluent, with or without such intervening treatment, can be returned to the fermentor as a part of the aqueous makeup, or as a substantial or almost total part of the aqueous makeup, to avoid waste disposal problems insofar as possible.

The microbial cells usually are killed if desired, by heat or chemical means, and this can be done before or after the separation of the cells from the fermentor effluent. The yeast cells are a valuable source of protein for man as well as beast. For human consumption, the cells can be treated as necessary to reduce the nucleic acid, but for animal feed purposes such tretment does not appear presently necessary.

The yeast cells are, in addition, a valuable source of enzymes for carrying out chemical conversions. In such cases, a broth of cells grown to high cell density according to the process of my invention can then be maintained in a resting state with no further manipulation required such as concentration step or the like in order to utilize the cells for carrying out enzyme conversions. Alternately, the dense broth of cells obtained in the process of my invention can be directly subjected to immobilization techniques such as described in "Methods in Enzymology", Vol. XLIV K. Moshach, ed., pp. 11–332. By achieving a high cellular density in the fermentation step, one avoids the need to concentrate the cells before immobilization, and thus the possibility of protein denaturation or loss of extracellular enzymes is greatly reduced. For example, the conversion of $C_3$–$C_6$ secondary alcohols to ketones disclosed by Hou, Patel and Laskin in U.S. Pat. Nos. 4,250,259, 4,268,630, and 4,269,940, is enhanced in the presence of the large number of cells obtained in the practice of my high cell density fermentation process, compared to the number of active cells made in a typical fermentation process.

Production of a high cell density broth is desirable whenever the yeast cells are to be used to promote secondary conversions, such as the oxidative reactions referred to above. Other examples are found in *Chemical Oxidations With Microorganisms* by G. S. Fonken and R. A. Johnson, (Dekker, N.Y., 1972). Anaerobic production of ethanol from glucose is most efficiently carried out by first producing a large number of cells in an aerobic fermentation, followed by the anaerobic conversion of glucose to ethanol (D. Williams and D. M. Munnecke, Biotech. and Bioeng. 23, 1813-1825 (1981). This overall conversion is enhanced by first producing the maximum feasible number of cells possible per liter of ferment in the first or aerobic stage, such as by employing my inventive high cell density method.

The oxidation of n-paraffins to diacids as described by Wegner in U.S. Pat. No. 3,796,630 is another application in which my high cell density method can be beneficial. Cells are grown on glucose or sucrose as carbon source and n-paraffins are oxidized at the same time to diacids. The more yeast cells produced, the greater the conversion of n-paraffins to diacids.

In accordance with my invention, employing high cell density operation, e.g., a cell density within the range of about 60 to 160, preferably about 70 to 150, grams of yeast cells, on a dried basis, per liter of ferment, can be obtained in high yield. If desired, the cells can be recovered from the fermentation admixture by centrifugation or other separation means. Also, if desired, the concentrated cells then can be washed such as by mixing with water, and separated such as by recentrifuging, or by adding water prior to or during centrifugation to substantially free the cells of mineral medium, and the washings including the separated mineral medium then can be returned to the fermentor as water and mineral medium makeup, thus substantially reducing or avoiding waste disposal problems. The recovered cells then can be employed in a chemical conversion process as described above, or simply dried to produce a dried product for future use. If desired, the high cell density fermentor effluent in total can be dried to produce a whole dried product of dried cells and residual water soluble substances including salts, and this whole-dried product used as a very useful animal feed of high protein-high salts character.

EXAMPLES

The following are descriptive runs employing the process in accordance with my discovery. Particular amounts of materials, or particular types of feedstocks employed, particular species or strains of yeast, should be considered as illustrative and not as limitative of my invention.

EXAMPLE I

In a run conducted under continuous aerobic fermentation process conditions, methanol and an aqueous mineral salts medium in a volume ratio of 30.15 to 69.85, respectively, were fed individually to a fermentor inoculated with the yeast *Pichia pastoris* Culture 21-2 deposited as NRRL Y-11431. No pre-conditioning medium or substrate was employed. The fermentor was a 4-liter fementor with a 2-liter liquid volume, with automatic pH, temperature, and level control. Agitation was provided by two impellers rotating at 1000–1200 rpm. The aeration rate was 1–1.5 volumes (at about atmospheric pressure and about 25° C.) per volume of ferment per minute of air supplemented with an including sufficient oxygen to maintain in the fermentation mixture an amount of dissolved oxygen equal to about 20 percent of that which would be dissolved in the fermentation mixture saturated with air at atmospheric pressure and about 30° C. Aqueous ammonium hydroxide (from 2 parts concentrated ammonium hydroxide and 1 part deionized water, by volume) was added at such a rate as to maintain the pH of the fermentation mixture at about 3.5.

The aqueous mineral salts medium employed was prepared by mixing, for each liter of solution, 12.5 mL 85 percent $H_3PO_4$, 2.5 g 85 percent KOH, 8.5 g KCl, 7.0 g $MgSo_4.7H_2O$, 1.5 g $CaCl_2.2H_2O$, 25 mL of trace mineral solution A, 25 mL of trace mineral solution B, 10 mL of a biotin-thiamine hydrochloride solution, about 0.08 mL of antifoam agent (Mazu DF-37C), and sufficient deionized water to make 1 liter of solution.

Trace mineral solution A was prepared by mixing, for each liter of solution, 4.8 g $FeCl_3.6H_2O$, 2.0 g $ZnSO_4.7H_2O$, 0.02 g $H_3BO_3$, 0.20 g $Na_2MoO_4.2H_2O$, 0.30 g $MnSO_4.H_2O$, 0.08 g KI, 0.06 g $CuSO_4.5H_2O$, 3 mL conc. $H_2SO_4$, and sufficient deionized water to make 1 liter of solution.

Trace mineral solution B was prepared by mixing, for each liter of solution, 2.0 g $FeCl_3.6H_2O$, 2.0 g $ZnSO_4.7H_2O$, 0.3 g $MnSO_4.H_2O$, 0.6 g $CuSO_4.5H_2O$, 2 mL conc. $H_2SO_4$, and sufficient deionized water to make 1 liter of solution.

The biotin-thiamine hydrochloride solution was prepared by mixing 2 mg biotin, 200 mg thiamine hydrochloride, and 50 mL deionized water.

The fermentation was conducted at about 30° C. and about atmospheric pressure, with a retention time of 7.0 hours.

Yeast cells were separated from the fermentation effluent by centrifugation, washed by suspension in water and recentrifugation, dried overnight at 100° C., and weighed. On a dried basis, the yeast cells were produced in a yield of 42.3 g per 100 g of methanol fed, the cell density being at the high level of 100.7 g of cells per liter of effluent.

EXAMPLE II

A further fermentation run was conducted using essentially the procedure described in Example I except that the composition of the aqueous mineral salts medium was somewhat different, the volume ratio of methanol to the aqueous mineral salts medium was 40.8 to 59.2, the aqueous ammonium hydroxide for pH control was prepared from 3 parts concentrated ammonium hydroxide and 1 part deionized water, by volume, and the fermentation retention time was 8.35 hours.

The aqueous mineral salts medium for use in this run was prepared by mixing, for each liter of solution, 20.0 mL 85 percent $H_3PO_4$, 4.0 g 85 percent KOH, 12.0 g KCL, 10.4 g $MgSO_4.7H_2O$, 2.4 g $CaCl_2.2H_2O$, 40 mL of the trace mineral solution A as described in Example I, 40 mL of the trace mineral solution B as described in Example I, 16 mL of the biotin-thiamine hydrochloride solution as described in Example I, about 0.08 mL of antifoam agent, and sufficient deionized water to make 1 liter of solution.

Yeast cells were separated from the fermentation effluent, washed, and dried as in Example I. On a dried basis, the yeast cells were produced in a yield of 41.4 g per 100 g of methanol fed, the cell density being at the very desirably high level of 133.3 g of cells per liter of effluent.

EXAMPLE III

A continuous aerobic fermentation process was conducted in the fermentor as described in Example I, this time inoculated with the yeast species *Hansenula polymorpha* Culture 21-3 deposited as NRRL Y-11432. To the fermentor was fed a mixture of methanol and aqueous mineral salts medium containing 300 mL methanol per liter total solution. The stirred fermentation mixture was aerated by passing into the fermentor 2 volumes (at about atmospheric pressure and about 25° C.) per volume of ferment per minute of air supplemented with and including sufficient oxygen to maintain in the fermentation mixture an amount of dissolved oxygen equal to about 20 percent of that which would be dissolved in the fermentation mixture saturated with air at atmospheric pressure and about 38° C.

Aqueous ammonium hydroxide (from 2 parts concentrated ammonium hydroxide and 1 part deionized water, by volume) was added at a rate to maintain the pH of the fermentation mixture at 3.7 to 4.1.

The mixture of methanol and aqueous mineral salts medium was prepared by mixing, for each liter of solution, 300 mL methanol, 6 mL 85 percent $H_3PO_4$, 3 g KCl, 4.5 g $MgSO_4.7H_2O$, 0.6 g $CaCl_2.2H_2O$, 0.3 g NaCl, 10 mL of trace mineral solution A as described in Example I, 10 mL of trace mineral solution B as described in Example I, 4 mL of the biotin-thiamine hydrochloride solution described in Example I, 4 drops of antifoam agent, and sufficient deionized water to make 1 liter of solution.

The fermentation was conducted at about 38° C. and about atmospheric pressure, with a retention time of 5.66 hours.

Yeast cells were separated from the fermentation effluent, washed, and dried as in Example I. On a dried basis, the yeast cells were produced in a yield of 31.0 g per 100 g of methanol fed, the cell density being at 73.3 g of cells per liter of effluent.

EXAMPLE IV

In a continuous aerobic fermentation process, methanol and an aqueous mineral medium in a volume ratio of 36.9 to 63.1, respectively, were fed individually to a fermentor inoculated with the yeast species *Pichia pastoris* Culture 21-1 deposited as NRRL Y-11430. The fermentor was a 1500-liter foam-filled fermentor with a liquid volume of about 600 liters, with automatic pH, temperature, and level control, and equipped with a draft tube. Agitation was provided by a turbine, below the draft tube, driven at 750 rpm. The aeration rate was about 1.6 volumes of air (at about 38 psig and about 25° C.) per volume of ferment in the fermentor per minute. Anhydrous ammonia was added at a rate to maintain the pH of the ferment mixture at about 3.5.

The primary aqueous mineral salts medium was prepared by mixing, for each liter of solution, 12.2 mL 75 percent $H_3PO_4$, 6.0 g KCl, 6.0 g $MgSO_4.7H_2O$, 0.8 g $CaCl_2.2H_2O$, 2.0 g 85 percent KOH, 2.0 mL of trace mineral solution C, 0.8 mL of a biotin-thiamine hydrochloride solution, and sufficient tap water to make 1 liter of solution, the tap water first having been treated with enough sodium thiosulfate to react with the free chlorine present therein.

Trace mineral solution C was prepared by mixing, for each liter of solution, 67.5 g $FeCl_3.6H_2O$, 18 g $ZnSO_4.7H_2O$, 5.0 g $MnSO_4.H_2O$, 6.0 g $CuSO_4.5H_2O$, 2.0 mL conc. $H_2SO_4$, and sufficient deionized water to make 1 liter of solution.

The biotin-thiamine hydrochloride solution was made by mixing the components in the ratio of 0.4 g biotin to 40 g thiamine hydrochloride to 1 liter deionized water.

The fermentation was conducted at 30° C. and 38 psig pressure, with a retention time of 12.7 hours.

Yeast cells were separated from the fermentation effluent by centrifugation, washed by suspension in water and recentrifugation, dried overnight at 100° C. at 100° C., and weighed. On a dried basis, the yeast cells were produced in a yield of 37 g per 100 g of methanol fed, the cell density being a very desirable 110.3 g of cells per liter of effluent.

EXAMPLE V

In a continuous aerobic fermentation process, methanol and an aqueous mineral salts medium in a volume ratio of 40 to 60, respectively, were fed individually to a fermentor inoculated with the yeast species *Pichia pastoris* Culture 21-1 deposited as NRRL Y-11430. The fermentor was a 1500-liter foam-filled fermentor with a liquid volume of about 610 liters, with automatic pH, temperature, and level control. Agitation was provided by two conventional paddle-type turbines driven at 1000 rpm. The aeration rate was about 4 volumes of air (at about 38 psig and about 25° C.) per volume of ferment in the fermentor per minute. Anhydrous ammonia was added at such a rate to maintain the pH of the fermentation mixture at about 3.5.

The aqueous mineral salts medium was prepared by mixing, with each liter of tap water, 15.86 mL 75 percent $H_3PO_4$, 9.53 g $K_2SO_4$, 7.8 g $MgSO_4.7H_2O$, 0.6 g $CaCl_2.2H_2O$, and 2.6 g 85 percent KOH. The trace mineral solution plug biotin was fed separately via the methanol stream at a rate of 10 mL per liter of methanol. The trace mineral solution plus biotin was prepared by mixing 780 mL trace mineral solution D, 20 mL water, 200 mL methanol and 0.032 g biotin.

Trace mineral solution D was prepared by mixing, for each liter of solution, 65 g $FeSO_4.7H_2O$, 20 g $ZnSO_4.7H_2O$, 3.0 g $MnSO_4.H_2O$, 6.0 g $CuSO_4.5H_2O$, 5.0 mL conc. $H_2SO_4$, and sufficient deionized water to make 1 liter of solution.

The aqueous mineral salts medium was fed at a rate of 31.5 liters per hour and the methanol at a rate of 21 liters per hour.

The fermentation was conducted at 30° C. and about 38 psig pressure, with a retention time of 11.6 hours.

For analytical purposes yeast cells were separated from the fermentation effluent by centrifugation, washed by suspension in water and recentrifugation, dried overnight at 100° C., and weighed. On a dried basis, the yeast cells were produced in a yield of 40.6 g per 100 g of methanol fed, the cell density being a very desirable 128.4 g of cells per liter of effluent. The total solids content of the ferment (effluent from the fermentor) was 134.7 g per liter, cells plus dissolved solids. The effluent from the fermentor was fed directly through a pasteurizer to kill the yeast and into a spray dryer without further concentration of treatment.

EXAMPLE VI

In a continuous aerobic fermentation process, methanol and an aqueous mineral salts medium in a volume ratio of 29 to 71, respectively, were fed individually to a fermentor inoculated with the yeast species *Hansenula polymorpha* NRRL Y-11170. The fermentor was a 1500-liter foam-filled fermentor with a liquid volume of about 560 liters, with automatic pH, temperature, and level control, and equipped with a draft tube. Agitation was provided by a turbine, below the draft tube, driven at 810 rpm. The aeration rate was about 5 volumes of air (at about 38 psig and about 25° C.) per volume of ferment in the fermentor per minute. Anhydrous ammonia was added at such a rate as to maintain the pH of the fermentation mixture at about 3.5.

The aqueous mineral salts medium was prepared by mixing 10.38 mL 75 percent $H_3PO_4$, 4.29 g KCl, 6.44 g $MgSO_4.7H_2O$, 0.86 g $CaCl_2.2H_2O$, 0.43 g NaCl, 3.0 mL of trace mineral solution C, and 0.64 mL of a biotin-thiamine hydrochloride solution in 1000 mL tap water, the tap water first having been treated with enough sodium thiosulfate to react with the free chlorine present therein.

The fermentation was conducted at 39°–40° C. and 38 psig pressure, with a retention time of 7.6 hours.

For analysis yeast cells were separated from the fermentation effluent by centrifugation, washed by suspension in water and recentrifugation, dried overnight at 100° C., and weighed. On a dried basis, the yeast cells were produced in a yield of 33.3 p per 100 g of methanol fed, the cell density being a desirable 76.2 g of cells per liter of effluent.

EXAMPLE VII

A further fermentation run was conducted using essentially the procedure described in Example I except employing a somewhat different composition of the aqueous mineral salts medium. The inoculum was *Pichia pastoris* NRRL Y-11430. Ethanol was employed as the carbon source in a volume ratio of 19 to 81 relative to the aqueous mineral medium. Anhydrous ammonia was added at such a rate sufficient to maintain the pH of the fermentation mixture at about 3.5. Fermentation retention time was 8.5 hours.

The aqueous mineral salts medium for use in this run was prepared by mixing, for each liter of solution, 15.9 mL 75 percent $H_3PO_4$, 0.6 g $CaSO_4.2H_2O$, 9.5 g $K_2SO_4$, 7.8 g $MgSO_4.7H_2O$, 2.6 g 85 percent KOH, 5.2 mL trace mineral solution E, and about 0.08 mL of antifoam agent (Mazu DF-37C).

Trace mineral solution E was prepared by mixing one liter of solution comprising: 65 g $FeSO_4.7H_2O$, 6.0 g $CuSO_4.5H_2O$, 24 g $ZnSO_4.7H_2O$, 3.0 g $MnSO_4.H_2O$, and 5 mL concentrated $H_2SO_4$, then withdrawing 780 ml of the thus prepared solution, adding 0.32 g biotin, and diluting to 1 liter with 200 mL methanol and 20 mL deionized water.

The fermentation was conducted at about 30° C. and about atmospheric pressure. Yeast cells were separated from the fermentation effluent by centrifugation, washed by suspension in water and recentrifugation, dried overnight at 100° C. and weighed. On a dried basis, the yeast cells were produced in a yield of 72.7 g per 100 g of ethanol fed, the cell density being a very desirable 106.8 g of cells per liter of effluent. The total solids content of the ferment (effluent from the fermentor) was 119.3 g per liter, cells plus dissolved solids.

EXAMPLE VIII

A further fermentation run was conducted using essentially the procedure described in Example VII except that glucose was employed as the carbon source, in a volume ratio of 26 to 74 relative to the aqueous mineral medium. Fermentation retention time was 9.8 hours.

The same aqueous mineral salts medium described for Example VII was employed for this run, except including trace mineral solution D, and omitting the antifoam agent.

The fermentation was conducted at about 30° C. and about atmospheric pressure. Yeast cells were separated from the fermentation effluent by centrifugation, dried overnight at 100° C. and weighed. On a dried basis, the yeast cells were produced in a yield of 46.6 g per gram of glucose fed, the cell density being a very desirable 120.0 g of cells per liter of effluent. The total solids content of the ferment (effluent from the fermentor) was 129.6 g per liter, cells plus dissolved solids.

EXAMPLE IX

In various runs, I have studied the effect of the volume percent carbon source as fed relative to the aqueous mineral media in the total fermentor feed on the maximum cell densities obtainable with, for example, *Pichia pastoris* NRRL Y-11430, and a specific substrate, such as methanol. In these studies, I have developed relationships tabulated below for methanol:

TABLE II

| Relative Volume % Methanol in Total Feed | Expected Cell Density[1] | Yield[2] | Actual Recovered Weight (total solids) |
|---|---|---|---|
| 10 | 33.2 | .42 | — |
| 20 | 64.8 | .41 | — |
| 40 | 126.4 | .40 | 133 |
| 50 | 154.1 | .39 | 165 |

[1]The expected cell density is a calculated value obtained by multiplying the number of grams of methanol fed per liter of feed times the yield.
[2]gm Single cell product/gm MeOH feed.

Yields of about 40 percent are obtained for growth of *Pichia pastoris* NRRL Y-11430, although yields of single cells are seen to decrease slightly at higher cell densities.

In order to accommodate the increased substrate feed, the concentration of mineral medium feed preferably is adjusted. Several factors are to be taken into account, such as the increased number of cells growing at higher cell densities are achieved and the reduced volume of water employed for the mineral feed. Thus, as shown below, the mineral medium feed that is employed for growth on 40 volume percent relative proportion of methanol feed may be about 6 times as concentrated as the mineral medium feed employed for growth on 10 volume percent relative proportion of methanol. On further increase of methanol feed to 50 volume percent, the mineral medium compositions preferably is adjusted to about 1.5 times the concentration employed with 40 volume percent relative proportion methanol feed.

TABLE III

Mineral Medium Adjustment as a Function of Methanol Feed

| Volume % Methanol in Feed | Mineral Medium Concentration | Mineral Concentration Increase per 10% Increase in MeOH Feed |
|---|---|---|
| 10 | 1 | — |
| 20 | 2.25 | 2.25 |
| 30 | 3.86 | 1.71 |
| 40 | 6.00 | 1.56 |
| 50 | 9.01 | 1.50 |

(3)Relative to 10% MeOH feed.

Simply put, if one considers as a constant the total volume of total feed (substrate such as methanol plus aqueous mineral media), it is apparent that as the substrate amount is increased, that the minerals fed must also increase.

NOVEL YEASTS

Discovery of yeasts with the capability of rapid growth and high productivity rates is distinctly advantageous.

I have discovered three very unique cultures of yeasts, namely *Pichia pastoris* my Culture 21-2, deposited as NRRL Y-11431; *Pichia pastoris* my Culture 21-1, deposited as NRRL Y-11430; and *Hansenula polymorpha* my Culture 21-3, deposited as NRRL Y-11432, with highly desirable and useful properties. These unique cultures grow particularly well at higher mineral salts levels and cell densities.

These three unique cultures of yeasts grow effectively with high productivity on oxygenated hydrocarbon feedstocks, particularly lower alcohols, most preferably methanol or ethanol. This is particularly noteworthy with regard to the new *Pichia pastoris* cultures since some cultures of the species *Pichia pastoris* simply cannot grow on methanol. These unique species are designated as follows:

| Culture Name | My Strain Designation | Depository Designation |
|---|---|---|
| *Pichia pastoris* | 21-2 | NRRL Y-11431 |
| *Pichia pastoris* | 21-1 | NRRL Y-11430 |
| *Hansenula polymorpha* | 21-3 | NRRL Y-11432 |

The designations NRRL Y-11431, NRRL Y-11430, and NRRL Y-11432 reflect the fact that I have deposited my novel yeast cultures 21-2, 21-1, and 21-3 with the official depository, United States Department of Agriculture, Agricultural Research Service, Northern Regional Research Laboratory, Peoria, Ill. 61604, by depositing therein two agar slant cultures of each, and have received from the depository the individual NRRL strain designations as indicated.

These unique cultures have been deposited in accordance with the procedures of the Department of Agriculture such that progeny of these strains will be available during pendency of this patent application to one determined by the Commissioner of Patents and Trademarks to be entitled thereto according to the *Rules of Practice in Patent Cases* and 35 U.S.C. 122. The deposits have been made in accordance with the Patent and Trademark Office practice such that all restrictions on availability to the public of progeny of the unique strains will be irrevocably removed upon granting of a patent of which these important strains are the subject, so that these strains will be available to provide samples for utilization in accordance with my invention. Thus, culture samples from these deposits or from my cultures from which the deposits were made provide strains derived from species of my discovery.

My invention provides in one aspect processes for culturing oxygenated hydrocarbon-assimilating microbial cells belonging to three new cultures or strains of microorganisms under aqueous aerobic culturing conditions. These strains have been classified:

|  | *Pichia pastoris* Culture 21-1 NRRL Y-11430 | *Pichia pastoris* Culture 21-2 NRRL Y-11431 | *Hansenula polymorpha* Culture 21-3 NRRL Y-11432 |
|---|---|---|---|
| Division | Ascomytina | Ascomytina | Ascomytina |
| Class | Hemiascomycetes | Hemiascomycetes | Hemiascomycetes |
| Order | Endomycetales | Endomycetales | Endomycetales |
| Family | Saccharomycetaceae | Saccharomycetaceae | Saccharomycetaceae |
| Genus | Pichia | Pichia | Hansenula |

The novel and unique microorganisms can be further characterized by properties as shown in the following tabulation:

|  | *Pichia pastoris* Culture 21-1 NRRL Y-11430 | *Pichia pastoris* Culture 21-2 NRRL Y-11431 | *Hansenula polymorpha* Culture 21-3 NRRL Y-11432 |
|---|---|---|---|
| Culture Property or Test Result[1] |  |  |  |
| Gram straining | + | + | + |
| Spore Forming | + | + | + |
| Aerobic | + | + | + |
| Approx. size, $\mu$ | 3–5 | 3–5 | 3–5 |
| Optimum temps., °C. | 30 | 30 | 38–40 |
| Optimum pH | 3.5–5.5 | 3.5–5.5 | 3.5–5.5 |
| Growth factors | Biotin | Biotin | Biotin and thiamine |
| Cell appearance on malt extract agar | Colonies turn deep tan with formation of hat-shaped spores | Form hat-shaped spores | Form hat-shaped spores |
| Colony appearance on YM agar | Cream colored; no pseudomycelium | Cream colored; no pseudomycelium | Cream colored; no pseudomycelium |
| Assimilation of sugars |  |  |  |
| Glucose | + | + | + |
| Galactose | W/L |  |  |
| L-Sorbose | — |  |  |
| Maltose | — |  |  |
| Sucrose | — |  |  |
| Cellobiose | — |  |  |
| Trehalose | — |  |  |
| Lactose | — |  |  |
| Melibiose | — |  |  |
| Raffinose | — |  |  |

-continued

| | Pichia pastoris Culture 21-1 NRRL Y-11430 | Pichia pastoris Culture 21-2 NRRL Y-11431 | Hansenula polymorpha Culture 21-3 NRRL Y-11432 |
|---|---|---|---|
| Melezitose | — | | |
| Inulin | — | | |
| Soluble Starch | W/L | | |
| Xylose | — | | |
| L-arabinose | — | | |
| D-arabinose | — | | |
| D-Ribose | — | | |
| L-Rhamnose | — | | |
| Ethyl alcohol | + | + | + |
| Methyl alcohol | + | + | + |
| Glycerol | + | | |
| Erythritol | — | | |
| Adonitol | — | | |
| Dulcitol | — | | |
| Mannitol | + | | |
| Sorbitol | + | | |
| Methyl-d-glucoside | — | | |
| Salicin | — | | |
| Inositol | — | | |
| Fermentation of sugars | | | |
| Glucose | + | + | + |
| Galactose | — | | |
| Sucrose | — | | |
| Lactose | — | | |
| Maltose | — | | |
| Raffinose | — | | |
| Trehalose | — | | |
| Nitrate | | | |
| Assimilation | — | | |
| Urease Activity | — | | |
| Arbutin split | | | |
| Pseudomycelium or hyphae formed | | | |
| on corn meal | — | | |
| on yeast agars | — | — | — |
| Guanine plus cytosine content of DNA | 40% | | |

+ = positive
− = negative
W/L = weak to latent reaction
(a) = if value not shown, means not determined.

Of course, as with all microorganisms, some of the characteristics may be subject to some variation depending on the medium and particular conditions.

The media recipes shown in my Examples can be used to culture the novel yeast species of my discovery and invention, though they will grow on other than methanol-containing substrates. These novel yeast cultures can be employed not only with the high salts-media feeds as herein described, but also can be employed under conventional fermentation conditions using a medium such as:

| Component | Amount |
|---|---|
| Medium IM-1 | |
| $KH_2PO_4$ | 5.0 g |
| $MgSO_4.7H_2O$ | 0.5 g |
| $CaCl_2.2H_2O$ | 0.2 g |
| KCl | 0.5 g |
| $(NH_4)_2SO_4$ | 3.0 g |
| Biotin | 0.04 mg |
| Thiamine | 4.0 mg |
| Trace mineral solution(a) | 2.5 mL |
| Water | 1,000 mL |
| Sterile methanol(b) to give | 0.5–1.0 vol % |

(a)See recipe below.
(b)Added just prior to use.

Trace Mineral Solution

| Component | Amount |
|---|---|
| $CuSO_4.5H_2O$ | 0.06 g |
| KI | 0.08 g |
| $MnSO_4.H_2O$ | 0.3 g |
| $Na_2MoO_4.2H_2O$ | 0.2 g |
| $H_3BO_3$ | 0.02 g |
| $ZnSO_4.7H_2O$ | 2.0 g |
| $FeCl_3.6H_2O$ | 4.8 g |
| Distilled water | 1,000 mL |
| $H_2SO_4$ (conc.) | 3 mL |

The disclosure, including data, illustrates the value and effectiveness of my invention. The examples, the knowledge and background of the field of the invention, general principles of microbiology, chemistry, and other applicable sciences, have formed the bases from which the broad descriptions of my invention, including the ranges of conditions and generic groups of operant components, have been developed, and which have formed the bases for my claims here appended.

I claim:

1. In a continuous process of biochemical conversion of a carbon energy substrate to products of fermentation comprising yeast cells and extracellular products which comprises culturing at least one yeast under aerobic aqueous fermentation conditions, in aqueous ferment comprising a cellular phase and an aqueous extracellular phase, in fermentation means employing effective amounts of a yeast-assimilable carbon energy substrate, assimilable nitrogen source, water, molecular oxygen, and mineral salts, and withdrawing said aqueous ferment as effluent for recovery therefrom of said products of fermentation, wherein the improvement comprises feeding said mineral salts to the aqueous ferment in amounts sufficient to maintain in said aqueous ferment the following elements in at least the designated weights per liter of aqueous ferment: P-1.9 g, K-1 g, Mg-0.15 g, Ca-0.06 g, S-0.1 g, Fe-6 mg, Zn-2 mg, Cu-0.6 mg, and Mn-0.6 mg, thereby producing at least one product of fermentation and maintaining a yeast cell density in said aqueous ferment of at least about 60 to 160 grams, on a dried basis, per liter of said aqueous ferment; said fermentative means being a fermenter free from physical means to remove liquid medium from said aqueous ferment without removing cells.

2. The process according to claim 1 wherein said yeast is selected from the group of genera consisting of Candida, Hansenula, Torulopsis, Saccharomyces, Pichia, Debaryomyces, and Brettanomyces.

3. The process according to claim 2 wherein the yeast is selected from the group of genera consisting of Candida, Hansenula, Torulopsis, Pichia, and Saccharomyces.

4. The process according to claim 2 wherein said yeast is selected from the group of species consisting of:

| | |
|---|---|
| Brettanomyces petrophilium, | Hansenula holstii, |
| Candida boidinii, | Pichia farinosa, |
| Candida lipolytica, | Pichia polymorpha, |
| Candida mycoderma, | Pichia membranaefaciens, |
| Candida utilis, | Pichia pinus, |
| Candida stellatoidea, | Pichia pastoris, |
| Candida robusta, | Pichia trebalophila, |
| Candida claussenii, | Saccharomyces cerevisiae, |
| Candida rugosa, | Saccharomyces fragilis, |

| -continued | |
|---|---|
| Candida tropicalis, | Saccharomyces rosei, |
| Debaryomyces hansenii, | Saccharomyces acidifaciens, |
| Hansenula minuta, | Saccharomyces elegans, |
| Hansenula saturnus, | Saccharomyces rouxii, |
| Hansenula californica, | Saccharomyces lactis, |
| Hansenula mrakii, | Torulopsis sonorensis, |
| Hansenula silvicola, | Torulopsis candida, |
| Hansenula polymorpha, | Torulopsis bolmii, |
| Hansenula wickerhamii, | Torulopsis versatilis, |
| Hansenula capsulata, | Torulopsis glabrata, |
| Hansenula glucozyma, | Torulopsis molishiana, |
| Hansenula henricii, | Torulopsis nemodendra, |
| Hansenula nonfermentans, | Torulopsis nitratophila, |
| Hansenula philodendra, | Torulopsis pinus, and |
| | Torulopsis bombicola. |

5. The process according to claim 4 maintaining in each liter of said aqueous ferment: P 1.9 to 20 g, K 1 to 20 g, Mg 0.15 to 3 g, Ca 0.06 to 1.6 g, S 0.1 to 8 g, Fe 6 to 140 mg, Zn 2 to 100 mg, Cu 0.6 to 16 mg, and Mn 0.6 to 20 mg.

6. The process according to claim 5 maintaining in each liter of said aqueous ferment about: P 2.2 to 10 g, K 1.5 to 10 g, Mg 0.3 to 1.2 g, Ca 0.08 to 0.8 g, S 0.2 to 5 g, Fe 9 to 80 mg, Zn 3 to 40 mg, Cu 1 to 10 mg, and Mn 0.9 to 8 mg.

7. The process according to claim 5 wherein said aqueous fermentation conditions include fermentation temperature in the range of 25° C. to 65° C., pH in the range of about 3 to 7, pressure in the range of about 0 to 150 psig, and fermentation time in the range of about 2 to 30 hours based on average retention.

8. The process according to claim 7 maintaining a cell density of about 70 to 150 grams, on a dried basis, per liter of aqueous ferment.

9. The process according to claim 7 maintaining a cellular yield of about 30 to 110 grams per 100 grams substrate charged.

10. The process according to claim 7 wherein said carbon energy substrate is an alcohol of 1 to 4 carbon atoms.

11. The process according to claim 7 wherein said alcohol is methanol.

12. The process according to claim 7 or 11 employing as said yeast Pichia pastoris NRRL Y-11430.

13. The process according to claim 7 or 11 employing as said yeast Pichia pastoris NRRL Y-11431.

14. The process according to claim 7 or 11 employing as said yeast Hansenula polymorpha NRRL Y-11432.

15. The process according to claim 7 further comprising the steps of:
(a) removing a stream of said aqueous ferment from said fermentation means,
(b) separating said removed stream of aqueous ferment into a stream of separated cells, and a stream comprising separated aqueous media containing residual dissolved minerals,
(c) water-washing said separated cells and thereby substantially separating said traces of mineral salts from the cells, leaving a wet cell mass,
(d) drying said wet cell mass to produce dried cells, and
(e) recycling the water-washings and separated aqueous media to said culturing to provide therein at least in part said makeup water and said mineral salts.

16. The process according to claim 7 further comprising the steps of:
removing a portion of said aqueous ferment as fermenter effluent containing said cellular phase, and aqueous extracellular phase including residual mineral salts, and
drying said aqueous ferment effluent containing said cellular phase and said aqueous phase,
thereby producing a dried cellular product containing residual water-soluble substances including salts.

17. The process of claim 7 further comprising the steps of:
(a) removing a stream of said aqueous ferment effluent from said fermentation means,
(b) centrifuging said removed aqueous ferment, thereby producing a stream of concentrated cells, and a stream of lean recycle mineral salts aqueous liquor,
(c) water-washing said concentrated cells to produce a stream of water-washings containing further residual mineral salts, and a stream of washed cells,
(d) drying said washed cells, and
(e) recycling at least a part of at least one of said lean recycle liquor and said water-washings to said aqueous ferment to provide therein at least a portion of said makeup water and mineral salts.

18. The process according to claim 5 further employing in said aqueous ferment at least one element selected from the group consisting of sodium, cobalt, molybdenum, boron, and selenium.

19. The process according to claim 18 further employing in said aqueous ferment at least one vitamin.

20. The process according to claim 19 wherein said vitamin is at least one of biotin or thiamine.

21. The process according to claim 20 wherein said mineral salts comprise a primary mineral salts medium and a trace mineral salts medium, and wherein said primary mineral salts medium supplies said P, K, Mg, S, and Ca; and said trace mineral salts medium furnishes said Fe, Zn, Mn, and Cu.

22. The process according to claim 21 wherein said carbon energy substrate is methanol or ethanol.

23. The process according to claim 22 further comprising the steps of:
admixing said vitamin with an aqueous solution of said methanol or ethanol,
adding said trace mineral salts medium thereto; and
feeding the resulting admixture into said aqueous ferment separately from said primary mineral salts medium.

24. The process according to claim 1 wherein said carbon energy substrate is selected from the group consisting of carbohydrates, alkenes, alcohols, ketones, aldehydes, acids, and esters, of 1 to 20 carbon atoms per molecule; $\alpha$-olefins of $C_{14}$ to $C_{18}$; and normal paraffins of 10 to 20 carbon atoms per molecule.

25. The process according to claim 24 wherein said carbon energy substrate is said carbohydrate, and is selected from the group consisting of glucose, fructose, galactose, lactose, sucrose, starch, dextrin, and mixtures.

26. The process according to claim 24 wherein said carbon energy substrate is said normal paraffin, and is selected from the group consisting of decane, undecane, dodecane, tridecane, tetradecane, pentadecane, hexadecane, octadecane, eicosane, and mixtures.

27. The process according to claim 24 wherein said carbon energy substrate is said alcohol, ketone, aldehyde, acid, or ester, and is selected from the group consisting of methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and mixtures.

28. In a fermentation process of producing yeast cells wherein at least one yeast is cultured in fermentation means characterized as being free from physical means to remove liquid medium from said aqueous ferment without removing cells, under aqueous aerobic fermentation conditions in an aqueous ferment comprising yeast cells and aqueous liquor employing yeast-assimilable carbon energy substrate, assimilable nitrogen source, water, oxygen, and mineral salts,
 removing aqueous ferment as effluent from said fermenter means, and
 recovering the so-produced yeast cells as a single cell protein product,
 wherein said carbon energy substrate is selected from the group consisting of carbohydrates, alcohols, ketones, aldehydes, acids, and esters, of 1 to 20 carbon atoms per molecule; and normal paraffins of 10 to 20 carbon atoms per molecule,
 wherein the improvement comprises:
 employing as said yeast a species selected from the group consisting of Pichia pastoris NRRL Y-11430, Pichia pastoris NRRL Y-11431, and Hansenula polymorpha NRRL Y-11432; and
 feeding sufficient said mineral salts to said aqueous ferment at a rate effective to maintain in said aqueous ferment the following elements in at least the designated minimum amounts, per liter of aqueous ferment: P 1.9 g, K 1 g, Mg 0.15 g, Ca 0.06 g, S 0.1 g, Fe 6 mg, Zn 2 mg, Cu 0.6 mg, and Mn 0.6 mg, thereby maintaining a cell density in said aqueous ferment of about 60 to 160 grams, on a dried basis, per liter of aqueous ferment.

29. The process according to claim 28 wherein said carbon energy substrate is said carbohydrate and is selected from the group consisting of glucose, fructose, galactose, lactose, sucrose, starch, dextrin, and mixtures.

30. The process according to claim 28 wherein said carbon energy substrate is said normal paraffin, and is selected from the group consisting of decane, undecane, dodecane, tridecane, tetradecane, pentadecane, hexadecane, octadecane, eicosane, and mixtures.

31. The process according to claim 28 wherein said carbon energy substrate is said alcohol, ketone, aldehyde, acid, or ester, and is selected from the group consisting of methanol, ethanol, ethylene glycol, propylene glycol, 1-propanol, 2-propanol, glycerol, 1-butanol, 2-butanol, 3-methyl-1-butanol, 1-pentanol, 2-hexanol, 1,7-heptanediol, 1-octanol, 2-decanol, 1-hexadecanol, 1-eicosanol, acetone, 2-butanone, 4-methyl-2-pentanone, 2-decanone, 3-pentadecanone, 2-eicosanone, formaldehyde, acetaldehyde, propionaldehyde, butyraldehyde, hexanal, 7-methyloctanal, tetradecanal, eicosanal, acetic acid, propionic acid, butyric acid, glutaric acid, 5-methylhexanoic acid, azelaic acid, dodecanoic acid, eicosanoic acid, methyl formate, methyl acetate, ethyl acetate, propyl butyrate, isopropyl hexanoate, hexyl 5-methyloctanoate, octyl dodecanoate, and mixtures.

32. The process according to claim 28 wherein said carbon energy substrate is an alcohol of 1 to 4 carbon atoms.

33. The process according to claim 32 maintaining in each liter of said aqueous ferment: P 1.9 to 20 g, K 1 to 20 g, Mg 0.15 to 3 g, Ca 0.06 to 1.6 g, S 0.1 to 8 g, Fe 6 to 140 mg, Zn 2 to 100 mg, Cu 0.6 to 16 mg, and Mn 0.6 to 20 mg.

34. The process according to claim 33 maintaining in each liter of said aqueous ferment: P 2.2 to 10 g, K 1.5 to 10 g, Mg 0.3 to 1.2 g, Ca 0.08 to 0.8 g, S 0.2 to 5 g, Fe 9 to 80 mg, Zn 3 to 40 mg, Cu 1 to 10 mg, and Mn 0.9 to 8 mg.

35. The process according to claim 34 wherein said alcohol is methanol or ethanol.

36. The process according to claim 35 further employing in said aqueous ferment at least one of the group consisting of sodium, cobalt, molybdenum, boron, and selenium.

37. The process according to claim 35 further employing in said aqueous ferment at least one vitamin.

38. The process according to claim 37 wherein said vitamin is biotin, thiamine, or both.

39. The process according to claim 38 wherein said mineral salts comprises a primary mineral salts medium and a trace mineral salts medium, and wherein said primary mineral salts medium supplies said P, K, Mg, S, and Ca, and said trace mineral salts medium furnishes said Fe, Zn, Mn, and Cu; and said process further comprises the steps of:
 admixing said vitamin with an aqueous solution of said methanol or ethanol,
 adding the trace mineral salts medium thereto, and
 feeding the resulting trace mineral salts medium/vitamin admixture into said aqueous ferment separately from said primary mineral salts medium.

40. The process according to claim 38 wherein said aqueous fermentation conditions include fermentation temperature in the range of 25° C. to 65° C., pH in the range of about 3 to 7, pressure in the range of about 0 to 150 psig, and fermentation time in the range of about 2 to 30 hours based on average retention.

41. The process according to claim 40 wherein said alcohol is methanol.

42. The process according to claim 41 further comprising the steps of:
 water-washing said aqueous ferment effluent by admixture thereof with water, separating aqueous liquor including mineral salts remaining in the separated media from the cells, leaving a wet cell mass, drying the wet cell mass to produce dried cells, and
 recycling the water-washings and separated mineral salts to said aqueous ferment to provide therein at least in part said makeup water and said mineral salts.

43. The process according to claim 41 further comprising the step of drying the aqueous ferment effluent from said culturing including cells and residual mineral salts, thereby producing a dried cell product containing residual water-soluble substances including mineral salts.

44. The process of claim 41 further comprising the steps of:

centrifuging said removed aqueous ferment effluent, thereby producing a stream of concentrated cells, and a stream of lean recycle liquor, water-washing said concentrated cells, separating water-washings from said cells to produce a stream of water-washings containing residual mineral salts, and a stream of washed cells, drying said washed cells, and recycling at least in part at least one of said lean recycle liquor and said water-washings to said aqueous ferment to provide therein at least a portion of said makeup water and said mineral salts.

45. The process according to claim 35 maintaining a cell density of about 70 to 150 grams, on a dried basis, per liter of aqueous ferment.

46. The process according to claim 35 maintaining a cellular yield of about 30 to 110 grams per 100 grams substrate charged.

47. A method of producing a protein material which comprises culturing a biologically pure yeast selected from the group consisting of *Pichia pastoris* NRRL Y-11430, *Pichia pastoris* NRRL Y-11431, or *Hansenula polymorpha* NRRL Y-11432, in an aqueous medium, employing an oxygenated hydrocarbon as carbon energy substrate, aerobic aqueous fermentation conditions, mineral salts, assimilable nitrogen source, and oxygen, and recovering from the resulting single cell microorganisms a protein material.

48. The process of claim 47 wherein said yeast is said *Pichia pastoris* NRRL Y-11430.

49. The process according to any of claims 48, 66, or 67 wherein said alcohol contains 1 to 4 carbon atoms per molecule.

50. The process according to claim 49 wherein said alcohol is methanol.

51. The process according to claim 47 wherein said yeast is said *Pichia pastoris* NRRL Y-11431.

52. The process according to claim 47 wherein said yeast is said *Hansenula polymorpha* NRRL Y-11432.

53. The process according to claim 47 wherein said carbon energy substrate is selected from the group consisting of alcohols, ketones, esters, ethers, acids, and aldehydes, which are substantially water-soluble and contain up to about 10 carbon atoms per molecule.

54. In a continuous process of biochemical conversion wherein a carbon energy substrate is converted to products of fermentation, which comprises culturing at least one yeast under aerobic aqueous fermentation conditions, in aqueous ferment comprising a cellular phase and an aqueous extracellular phase, employing a yeast-assimilable carbon energy substrate, assimilable nitrogen source, water, molecular oxygen, and mineral salts, wherein the improvement comprises:

employing a yeast selected from the group consisting of *Pichia pastoris* NRRL Y-11430, *Pichia pastoris* NRRL Y-11431, and *Hansenula polymorpha* NRRL Y-11432, and feeding said mineral salts to said aqueous ferment in an amount sufficient to maintain in said aqueous ferment the following elements in at least the designated amounts per liter of aqueous ferment: P 1.9 g, K 1 g, Mg 0.15 g, Ca 0.06 g, S 0.1 g, Fe 6 mg, Zn 2 mg, Cu 0.6 mg, and Mn 0.6 mg, and said carbon energy substrate in amounts required for maximum growth of cells, maintaining a yeast cell density in said aqueous ferment of about 60 to 160 grams on a dried basis per liter of said aqueous ferment, and producing at least one product of fermentation.

55. The process of claim 54 wherein said carbon energy substrate is methanol.

56. The process according to claim 55 wherein said biochemical conversion employs as said carbon energy substrate methanol, ethanol, or glucose, and produces fermentation products comprising carbon dioxide and single cell protein.

57. A fermentation process of producing yeast protein product, which comprises culturing a yeast under aqueous aerobic fermentation conditions, in aqueous ferment comprising yeast cells and aqueous liquor, employing yeast-assimilable carbon energy substrate, assimilable nitrogen source, water, oxygen, and mineral salts comprising a primary salts medium and a trace mineral salts, feeding sufficient said mineral salts to said aqueous ferment to maintain the following elements in at least the minimum amount, per liter of aqueous ferment: P 1.9 g, K 1 g, Mg 0.15 g, Ca 0.06 g, S 0.1 g, Fe 6 mg, Zn 2 mg, Cu 0.6 mg, and Mn 0.6 mg, thereby maintaining a cell density in said aqueous ferment of about 60 to 160 grams, on a dried basis, per liter of aqueous ferment, employing a fermenter characterized as being free from physical means to remove liquid medium from said aqueous ferment without removing cells, and recovering the resulting yeast microorganisms, wherein said carbon energy substrate is selected from the group consisting of carbohydrates, alcohols, ketones, aldehydes, acids, and esters, of 1 to 20 carbon atoms per molecule; and normal paraffins of 10 to 20 carbon atoms per molecule.

58. The process according to claim 57 wherein said yeast is selected from the group consisting of *Pichia pastoris* NRRL Y-11430, *Pichia pastoris* NRRL Y-11431, and *Hansenula polymorpha* NRRL Y-11432, and said carbon energy substrate is methanol or ethanol.

* * * * *

UNITED STATES PATENT AND TRADEMARK OFFICE
CERTIFICATE OF CORRECTION

PATENT NO. : U.S. 4,414,329

DATED : November 8, 1983

INVENTOR(S) : Eugene H. Wegner

It is certified that error appears in the above-identified patent and that said Letters Patent are hereby corrected as shown below:

Column 27, lines 31 and 32, Claim 49, lines 1 and 2 should read:

--- any of claims 48, 51, or 52 ---.

Signed and Sealed this

Fourteenth Day of February 1984

[SEAL]

Attest:

Attesting Officer

GERALD J. MOSSINGHOFF

Commissioner of Patents and Trademarks